United States Patent
Ezoe et al.

(10) Patent No.: US 12,029,569 B2
(45) Date of Patent: Jul. 9, 2024

(54) PORTABLE ELECTROCARDIOGRAPHIC WAVEFORM MEASUREMENT DEVICE, INFORMATION MANAGEMENT SYSTEM, METHOD OF CONTROLLING PORTABLE ELECTROCARDIOGRAPHIC WAVEFORM MEASUREMENT DEVICE, AND NON-TRANSITORY RECORDING MEDIUM INCLUDING PROGRAM RECORDED THEREIN

(71) Applicant: OMRON HEALTHCARE Co., Ltd., Kyoto (JP)

(72) Inventors: Mika Ezoe, Kyoto (JP); Mitsuru Samejima, Kyoto (JP); Shinya Kodaka, Kyoto (JP); Miho Hiraki, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 232 days.

(21) Appl. No.: 17/804,886

(22) Filed: Jun. 1, 2022

(65) Prior Publication Data
US 2022/0361797 A1 Nov. 17, 2022

Related U.S. Application Data

(63) Continuation of application No. PCT/JP2020/045632, filed on Dec. 8, 2020.

(30) Foreign Application Priority Data

Dec. 20, 2019 (JP) .................................. 2019-230660

(51) Int. Cl.
G08B 21/00 (2006.01)
A61B 5/332 (2021.01)
(Continued)

(52) U.S. Cl.
CPC ........ *A61B 5/332* (2021.01); *G01R 19/16542* (2013.01); *G01R 31/3646* (2019.01)

(58) Field of Classification Search
CPC .............. A61B 5/332; G01R 19/16542; G01R 31/3646
(Continued)

(56) References Cited

U.S. PATENT DOCUMENTS

2007/0149886 A1* 6/2007 Kohls .................... A61B 5/411
600/509
2008/0082015 A1* 4/2008 Kohls .................... A61B 5/352
600/509

(Continued)

FOREIGN PATENT DOCUMENTS

EP 3575005 A1 12/2019
JP 2002-002179 A 1/2002
(Continued)

OTHER PUBLICATIONS

International Search Report for International Application No. PCT/JP2020/045632, Dated Feb. 22, 2021.
(Continued)

*Primary Examiner* — Naomi J Small
(74) *Attorney, Agent, or Firm* — Colson Law Group, PLLC

(57) ABSTRACT

A portable electrocardiographic waveform measurement device using a battery as a power source includes a plurality of electrodes configured to measure an electrocardiographic waveform, a vibration unit configured to generate vibration, and a control unit configured to execute measurement processing for the electrocardiographic waveform. The control unit vibrates the vibration unit in a first vibration pattern when the measurement processing for the electrocardiographic waveform is started, and vibrates the vibration unit
(Continued)

in a second vibration pattern when the measurement processing for the electrocardiographic waveform is ended.

10 Claims, 16 Drawing Sheets

(51) Int. Cl.
*G01R 19/165* (2006.01)
*G01R 31/36* (2020.01)

(58) Field of Classification Search
USPC ..................................................... 340/636.1
See application file for complete search history.

(56) References Cited

U.S. PATENT DOCUMENTS

2010/0076331 A1* 3/2010 Chan .................... A61B 5/681
600/509
2016/0088132 A1* 3/2016 Kranz .................... G16H 40/67
455/556.1
2017/0185737 A1* 6/2017 Kovacs .............. A61B 5/02416
2019/0358464 A1* 11/2019 Volosin .................. A61B 5/024

FOREIGN PATENT DOCUMENTS

| JP | 2005-000420 A | 1/2005 |
| JP | 2008-086770 A | 4/2008 |
| JP | 2012-45195 A | 3/2012 |

OTHER PUBLICATIONS

International Preliminary Report on Patentability for International Application No. PCT/JP2020/045632, Dated Oct. 8, 2021.

* cited by examiner

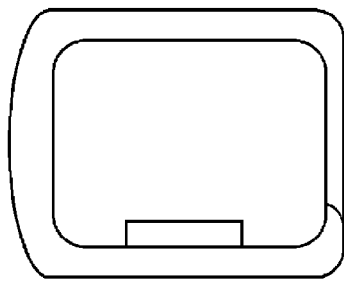
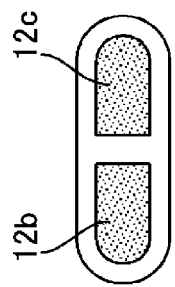
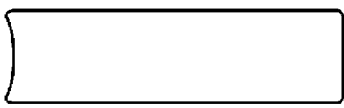
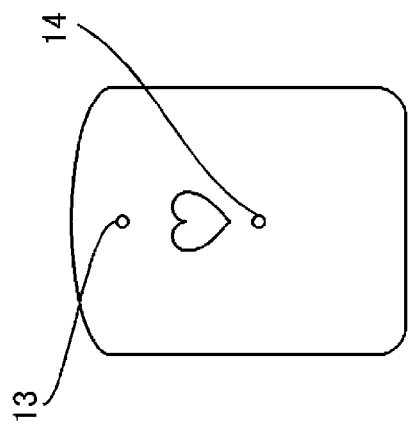
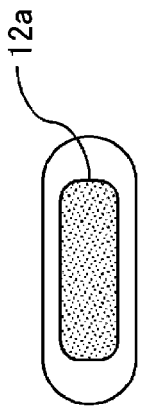
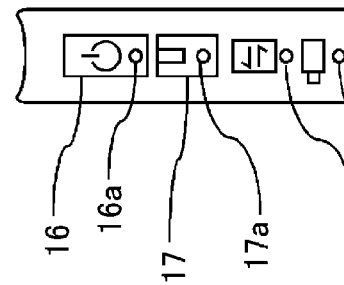

PORTABLE ELECTROCARDIOGRAPHIC WAVEFORM MEASUREMENT DEVICE, INFORMATION MANAGEMENT SYSTEM, METHOD OF CONTROLLING PORTABLE ELECTROCARDIOGRAPHIC WAVEFORM MEASUREMENT DEVICE, AND NON-TRANSITORY RECORDING MEDIUM INCLUDING PROGRAM RECORDED THEREIN

CROSS-REFERENCE TO RELATED APPLICATIONS

This application is the U.S. national stage application filed pursuant to 35 U.S.C. 365(c) and 120 as a continuation of International Patent Application No. PCT/JP2020/045632, filed Dec. 8, 2020, which application claims priority to Japan Patent Application No. 2019-230660, filed Dec. 20, 2019, which applications are incorporated herein by reference in their entireties.

TECHNICAL FIELD

The present invention belongs to a technical field related to healthcare, and particularly relates to a portable electrocardiographic waveform measurement device, an information management system, a control method for the portable electrocardiographic waveform measurement device, and a program.

BACKGROUND ART

In recent years, health management has been becoming more and more common in which information related to individual bodies and health (hereinafter also referred to as "biological information") such as a blood pressure value and an electrocardiographic waveform is measured using a measurement device, with measurement results recorded and analyzed by an information processing terminal.

As an example of a measurement device as described above, a portable electrocardiographic measurement device has been proposed that measures, in everyday life, an electrocardiographic waveform immediately when an abnormality such as chest pain or palpitation occurs, and the portable electrocardiographic measurement device is expected to contribute to early detection and appropriate treatment of a heart disease (e.g., Patent Document 1).

In a case where such a portable electrocardiographic measurement device is used to make measurement with chest leads, the measurement is naturally performed with clothes on. However, in a case where the device is covered by the clothes, then in that state, a display processing unit is prevented from being viewed, leading to difficulty in confirming events such as start and end of the measurement and occurrence of an abnormality such as a measurement error.

On the other hand, the following have been proposed: a technology using sound or vibration to give notice of a health abnormality in response to observing the health abnormality (Patent Document 2), a technology using sound or vibration to give notice of the start and end of electrocardiographic measurement (Patent Document 3), a technology using vibration to give notice of an abnormality in the electrocardiographic waveform or a decrease in battery voltage (Patent Document 4), and the like.

CITATION LIST

Patent Literature

Patent Document 1: JP 2005-420 A
Patent Document 2: JP 2002-02179 A
Patent Document 3: JP 2008-86770 A
Patent Document 4: JP 2012-45195 A

SUMMARY OF INVENTION

However, even the technologies described in Patent Documents 2 to 4 present a problem in that the sound notification is unfavorable in a situation where generation of sound is to be refrained from and in that even with the vibration notification, which event is occurring cannot be determined simply by using the vibration.

In view of the above-described known technologies, an object of the present invention is to provide a technology in which, in a portable electrocardiographic measurement device, the times to start and end electrocardiographic measurement processing can be recognized while being clearly identified with no need to view the portable electrocardiographic measurement device.

In order to achieve the object described above, a portable electrocardiographic waveform measurement device according to an aspect of the present invention includes a plurality of electrodes configured to measure an electrocardiographic waveform, a vibration unit configured to generate vibration, and a control unit configured to execute measurement processing for the electrocardiographic waveform. The portable electrocardiographic waveform measurement device uses a battery as a power source. The control unit vibrates the vibration unit in a first vibration pattern when the measurement processing for the electrocardiographic waveform is started, and vibrates the vibration unit in a second vibration pattern when the measurement processing for the electrocardiographic waveform is ended.

In such a configuration, the vibration pattern used when measurement is started is different from the vibration pattern used when the measurement is ended, allowing the times to start and end the measurement to be recognized without depending on a visual sense or an auditory sense, with the times clearly identified.

Additionally, the control unit may vibrate the vibration unit in a third vibration pattern in a case where the measurement processing for the electrocardiographic waveform fails to complete successfully. In such a configuration, even in a case where an abnormality occurs in the measurement processing, the abnormality can be recognized without depending on the visual sense or the auditory sense.

Further, the portable electrocardiographic waveform measurement device further includes a communication unit configured to communicate with the information processing terminal, and the control unit may be configured to further execute communication processing with the information processing terminal, and to vibrate the vibration unit in a fourth vibration pattern in a case where an abnormality occurs in communication with the information processing terminal during the communication processing.

According to such a configuration, the portable electrocardiographic measurement device can be used in cooperation with the information processing terminal, and in a case where a communication error occurs between portable electrocardiographic measurement device and the information processing terminal, the communication error can be recognized without depending on the visual sense or the auditory sense.

Additionally, the control unit may be configured to further execute communication setting processing for switching the communication unit between an ON state in which communication is enabled and an OFF state in which communication is disabled. In addition, the control unit may be configured to vibrate the vibration unit in a fifth vibration pattern in a case where the control unit executes the processing for switching the communication unit to the ON state. Additionally, the control unit may be configured to vibrate the vibration unit in a sixth vibration pattern in a case where the control unit executes the processing for switching the communication unit to the OFF state.

Such a configuration allows switching of the communication settings of the portable electrocardiographic measurement device to be recognized without depending on the visual sense or the auditory sense.

Additionally, the portable electrocardiographic measurement device may further include an input unit configured to receive input from a user, and the control unit may vibrate the vibration unit in a seventh vibration pattern in a case where the communication unit is in the OFF state when the control unit receives, via the input unit, an indication to execute the communication processing.

In addition, the portable electrocardiographic measurement device further includes a storage unit configured to store at least information for device registration for the information processing terminal, and the control unit may be configured to further execute pairing processing for device registration of the information processing terminal, and to vibrate the vibration unit in an eighth vibration pattern when the pairing processing is started. Such a configuration allows a transition to a pairing mode to be easily recognized without depending on the visual sense or the auditory sense.

Additionally, the control unit may be configured to vibrate the vibration unit in a ninth vibration pattern in a case where a discharge voltage of the battery is equal to or less than a predetermined threshold.

Additionally, the portable electrocardiographic measurement device may include an LED display unit, and the control unit may be configured to blink the LED display unit in a predetermined blinking pattern associated with each of the above-described vibration patterns when the control unit vibrates the vibration unit. In such a configuration, in a case where blinking of the LED display processing unit is visible (even through clothes), the occurrence and contents of an event can be more clearly recognized.

Additionally, an information management system according to the present invention includes the portable electrocardiographic waveform measurement device including a communication unit, and an information processing terminal including a communication unit configured to communicate with the communication unit of the portable electrocardiographic waveform measurement device.

Additionally, a control method for a portable electrocardiographic waveform measurement device according to the present invention is a method for controlling a portable electrocardiographic waveform measurement device including a vibration unit configured to cause vibration. The method includes the steps of: vibrating the vibration unit in a first vibration pattern when measurement of an electrocardiographic waveform is started, performing the measurement of the electrocardiographic waveform, and vibrating the vibration unit in a second vibration pattern when the measurement of the electrocardiographic waveform is ended.

In addition, the present invention can be considered as a program for causing an electrocardiographic measurement device to execute the above-described method, and a computer-readable recording medium including such a program recorded therein in a non-transitory manner.

Also, the configurations and processing operations described above can be combined with one another to constitute the present invention unless the combination leads to contradiction.

Advantageous Effects of Invention

The present invention provides a technology in which, in a portable electrocardiographic measurement device, the times to start and end electrocardiographic measurement processing can be recognized while being clearly identified with no need to view the portable electrocardiographic measurement device.

BRIEF DESCRIPTION OF DRAWINGS

FIG. 1(A) is a front view illustrating a configuration of a portable electrocardiographic measurement device according to an embodiment. FIG. 1(B) is a rear view illustrating the configuration of the portable electrocardiographic measurement device according to the embodiment. FIG. 1(C) is a left side view illustrating the configuration of the portable electrocardiographic measurement device according to the embodiment. FIG. 1(D) is a right side view illustrating the configuration of the portable electrocardiographic measurement device according to the embodiment. FIG. 1(E) is a plan view illustrating the configuration of the portable electrocardiographic measurement device according to the embodiment. FIG. 1(F) is a bottom view illustrating the configuration of the portable electrocardiographic measurement device according to the embodiment.

DESCRIPTION OF EMBODIMENTS

Figure 2:
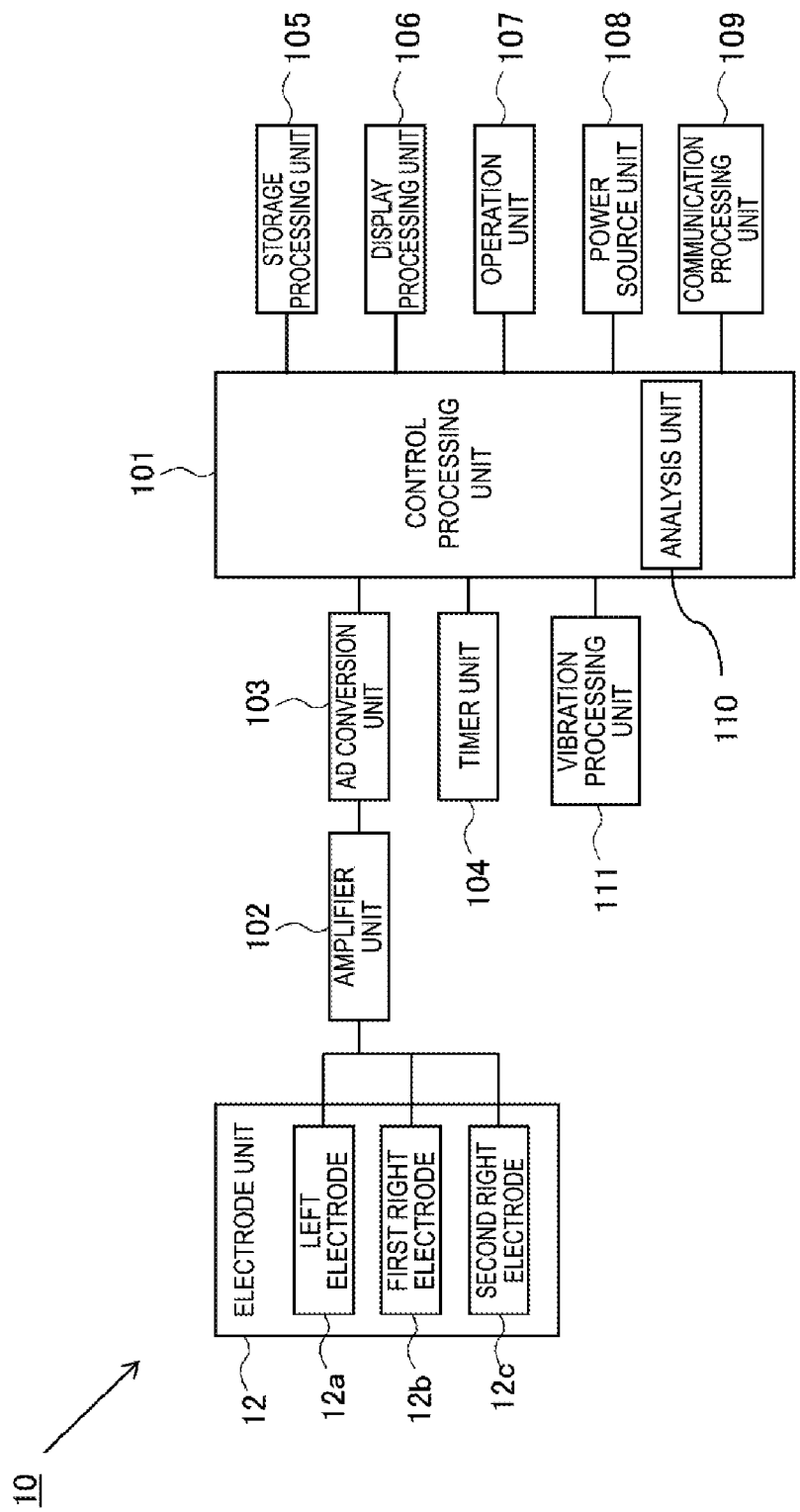
FIG. 2 is a block diagram illustrating a functional configuration of the portable electrocardiographic measurement device according to the embodiment.

First Embodiment: Embodiments of the present invention will be specifically described below with reference to the drawings. It should be noted that the dimension, material, shape, relative arrangement and the like of the components described in the present embodiment are not intended to limit the scope of this invention to them alone, unless otherwise stated.

Electrocardiographic Measurement Device: FIGS. 1(A) through 1(F) are diagrams illustrating a configuration of a portable electrocardiograph 10 according to the present embodiment. FIG. 1(A) is a front view illustrating the front of the body. Similarly, FIG. 1(B) is a rear view, FIG. 1(C) is a left side view, FIG. 1(D) is a right side view, FIG. 1(E) is a plan view, and FIG. 1(F) is a bottom view.

A bottom surface of the portable electrocardiograph 10 is provided with a left electrode 12a brought into contact with the left side of the body during electrocardiographic measurement. A top surface side of the portable electrocardiograph 10, opposite to the bottom surface, is provided with a first right electrode 12b similarly brought into contact with the center of the right-hand index finger and a second right electrode 12c brought into contact with the base of the right-hand index finger. Note that the first right electrode 12b functions as a GND electrode.

During electrocardiographic measurement, the portable electrocardiograph 10 is held by the right hand, and the right-hand index finger is placed on the top surface portion of the portable electrocardiograph 10 in proper contact with the first right electrode 12b and the second right electrode 12c. Furthermore, the left electrode 12a is then brought into contact with the skin at a location corresponding to a desired lead type. For example, in a case where measurement is performed by a so-called lead I, the left electrode 12a is brought into contact with the palm of the left hand. In a case where measurement is performed by a so-called lead V4, the left electrode 12a is brought into contact with the skin slightly leftward of the epigastric region of the left thorax and below the nipple.

In addition, various operation units and indicators are disposed on a left side surface of the portable electrocardiograph 10. Specifically, the left side surface includes a measurement switch 16, a measurement mode LED 16a, a Bluetooth (trade name) low energy (BLE) communication button 17, a BLE communication LED 17a, an available memory display LED 18, a battery change LED 19, and the like.

Additionally, a front surface of the portable electrocardiograph 10 is provided with a measurement state notification LED 13 and an analysis result notification LED 14, and a housing port (not illustrated) for the battery and a battery cover 15 that covers the housing port are disposed on a rear surface of the portable electrocardiograph 10.

FIG. 2 illustrates a block diagram illustrating a functional configuration of the portable electrocardiograph 10. As illustrated in FIG. 2, the portable electrocardiograph 10 includes function units including a control processing unit 101, an electrode unit 12, an amplifier unit 102, an analog to digital (AD) conversion unit 103, a timer unit 104, a storage processing unit 105, a display processing unit 106, an operation unit 107, a power supply unit 108, a communication processing unit 109, an analysis unit 110, and a vibration processing unit 111.

The control processing unit 101 manages the control of the portable electrocardiograph 10, and includes a central processing unit (CPU) and the like, for example. In response to receiving operation of the user via the operation unit 107, the control processing unit 101 controls each component of the portable electrocardiograph 10 to execute various processing operations such as electrocardiographic measurement and information communication in accordance with a predetermined program. Note that the predetermined program is stored in the storage processing unit 105 described below.

Additionally, the control processing unit 101 includes, as a functional module, the analysis unit 110 analyzing electrocardiographic waveforms. The analysis unit 110 analyzes the measured electrocardiographic waveform for the presence of disturbance or the like, and outputs a result indicating whether the electrocardiographic waveform obtained at least during measurement is normal.

The electrode unit 12 includes the left electrode 12a, the first right electrode 12b, and the second right electrode 12c, and functions as a sensor for detecting an electrocardiographic waveform. The amplifier unit 102 functions to amplify signals output from the electrode unit 12. The AD conversion unit 103 functions to convert an analog signal amplified by the amplifier unit 102 into a digital signal and to transmit the converted signal to the control processing unit 101.

The timer unit 104 functions to measure time with reference to a real time clock (RTC, not illustrated). As described below, for example, the period of time until the end of measurement is counted and output during the electrocardiographic measurement.

The storage processing unit 105 includes a main memory (not illustrated) such as a random access memory (RAM) and stores various types of information such as application programs, measured electrocardiographic waveforms, and analysis results. In addition to the RAM, for example, a long-term storage medium such as a flash memory may be provided.

The display processing unit 106 includes light emitting elements such as the measurement mode LED 16a, the BLE communication LED 17a, the available memory LED 18, and the battery change LED 19 described above, and informs the user of the state of the device and the occurrence of an event by lighting, blinking, or the like of the LEDs. Additionally, the operation unit 107 includes the measurement switch 16, the communication button 17, and the like, and functions to receive an input operation from the user and to cause the control processing unit 101 to execute processing in accordance with the operation.

The power supply unit 108 includes a battery (not illustrated) that supplies power required for operation of the device. The battery may be, for example, a secondary battery such as a lithium ion battery, or a primary battery.

The communication processing unit 109 includes an antenna for wireless communication (not illustrated), and functions to communicate with another device such as an information processing terminal described below at least by BLE communication. Additionally, a terminal may be provided for wired communication.

The vibration processing unit 111 includes a vibrator (not illustrated) made from a small motor or the like, and functions to cause vibration in a predetermined pattern to notify the user of the occurrence of a predetermined event corresponding to the pattern, as described below.

Electrocardiographic Measurement Using Portable Electrocardiograph

Figure 3:
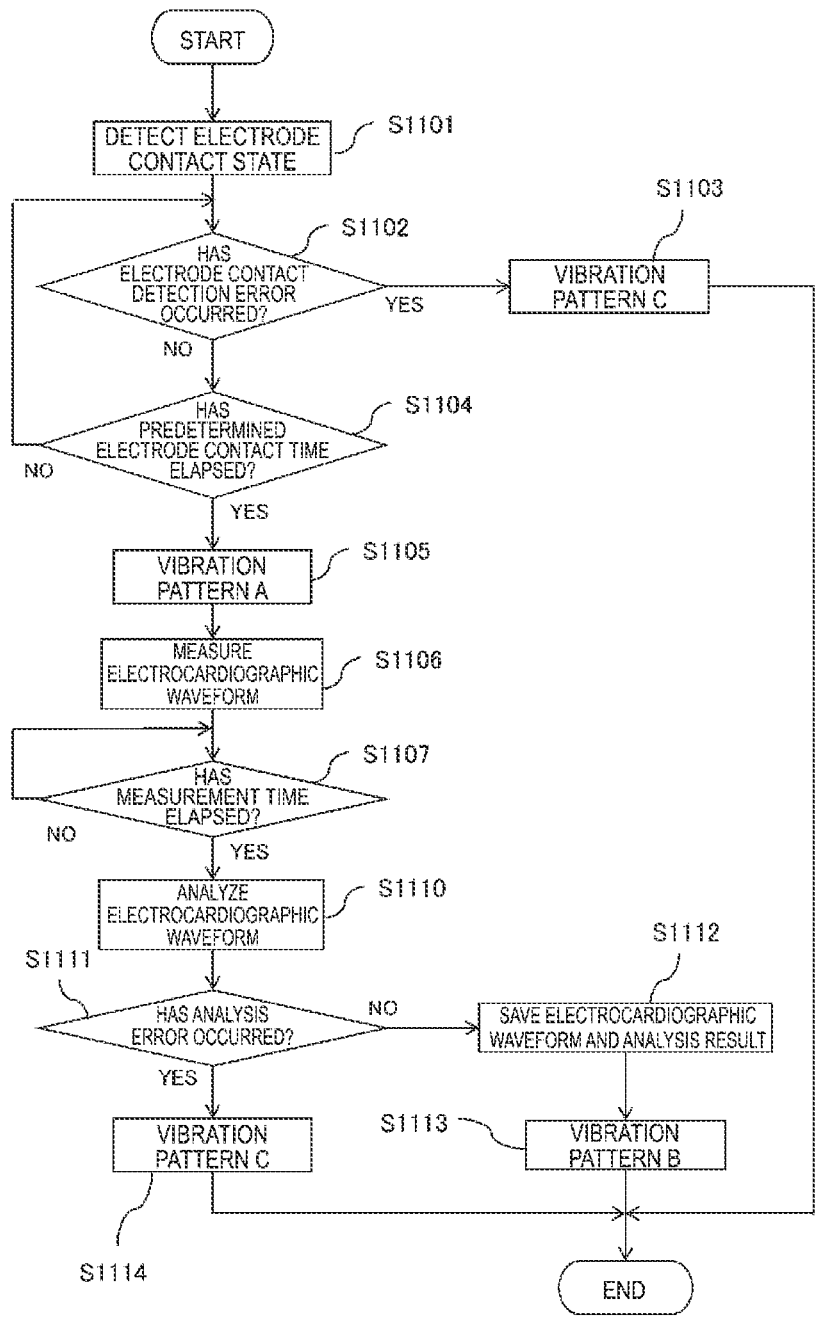
FIG. 3 is a flowchart illustrating a flow of electrocardiograph measurement processing in the portable electrocardiographic measurement device according to the embodiment.

Now, a description will be given for operation of the portable electrocardiograph 10 that is performed when the electrocardiographic measurement is performed. FIG. 3 is a flowchart illustrating a procedure of processing executed when electrocardiographic measurement is performed using the portable electrocardiograph 10 according to the present embodiment.

Before measurement of an electrocardiographic waveform, when the user presses the measurement switch 16 down, the device is powered on to execute a measurement mode, and the measurement mode LED 16a is lighted to indicate that the measurement mode is in execution. With the measurement mode in execution, the user holds the portable electrocardiograph 10 in the right hand, with the right-hand index finger in contact with the first right electrode 12b and the second right electrode 12c, and with the left electrode 12a in contact with the skin at a location to be measured. Then, the control processing unit 101 detects the contact state via the electrode unit 12 (S1101). Subsequently, the control processing unit 101 executes processing for determining whether the electrodes are in proper contact with the measurement site (i.e., whether any contact detection error is occurring) (S1102), and in response to determining that a contact detection error is occurring, the control processing unit 101 vibrates the vibration processing unit 111 in a predetermined vibration pattern (hereinafter referred to as a pattern C) meaning that the measurement has not been successful (S1103), and ends the measurement processing. Note that at this time, for example, the measurement state notification LED 13 may be blinked in a predetermined pattern associated with the pattern C.

On the other hand, in step S1102, in response to determining that no contact detection error is occurring, the control processing unit 101 then executes processing for determining whether a predetermined time has elapsed with the electrodes in proper contact (S1104). Here, in response to determining that the predetermined time has not elapsed, then the control processing unit 101 returns to step S1102, and repeats similar processing. On the other hand, in response to determining that the predetermined time has elapsed, the control processing unit 101 vibrates the vibration processing unit 111 in a predetermined vibration pattern (hereinafter referred to as a pattern A) meaning that electrocardiographic measurement is to be started (S1105), and executes the actual electrocardiographic measurement (S1106). Note that the data of the measured electrocardiographic waveform is stored in the storage processing unit 105. In step S1105, for example, the measurement state notification LED 13 may be blinked in a predetermined pattern associated with the pattern A.

Then, the control processing unit 101 executes processing for determining whether the elapsed time of the electrocardiographic measurement has reached a predetermined value (for example, 30 seconds) (step S1107). Here, in response to determining that the predetermined time has not elapsed, the control processing unit 101 repeats the processing in step S1107. On the other hand, in response to the control processing unit 101 determining that the predetermined measurement time has elapsed, the analysis unit 110 of the control processing unit 101 analyzes the electrocardiographic waveform data stored in the storage processing unit 105 (S1110). Then, the control processing unit 101 executes processing for determining whether the electrocardiographic waveform has been properly analyzed (i.e., whether an analysis error has occurred) (S1111), and in response to determining that an analysis error has occurred, the control processing unit 101 vibrates the vibration processing unit 111 in the pattern C (S1114), and ends the measurement processing.

On the other hand, in response to determining in step S1111 that the analysis has been properly performed, the control processing unit 101 saves an analysis result and electrocardiographic waveform data in the storage processing unit 105 (S1112), and vibrates the vibration processing unit 111 in a predetermined vibration pattern (hereinafter referred to as a pattern B) meaning that a series of processing operations related to the measurement is successfully ended. The control processing unit 101 then ends the series of processing operations. In this regard, for example, the measurement state notification LED 13 may be blinked in a predetermined pattern associated with the pattern B.

As described above, in the portable electrocardiograph 10 according to the present embodiment, the vibration processing unit 111 vibrates in the different patterns when the acquisition of the electrocardiographic waveform data is started, when the measurement processing is successfully ended, and when the measurement is ended due to an error. Thus, the user can recognize the occurrence and contents of an event related to the measurement processing of the portable electrocardiograph 10 from a difference in the vibration pattern without viewing the display processing unit 106. Thus, even in a case where electrocardiographic measurement with chest leads is performed on the user keeping clothes on, timings for starting and ending the electrocardiographic measurement can be easily recognized.

Figure 4:
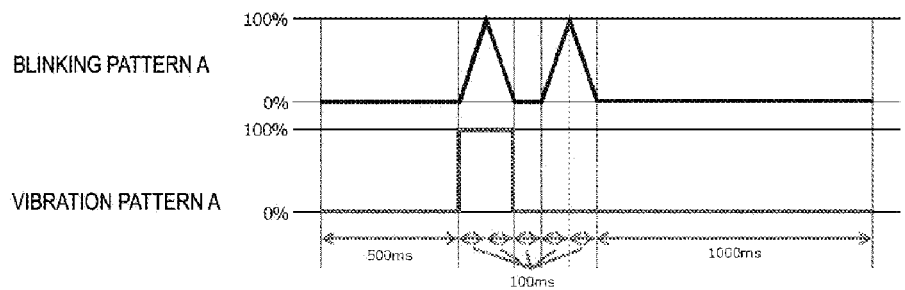
FIG. 4(A) is a first diagram illustrating an example of a vibration pattern and an LED blink pattern in the portable electrocardiographic measurement device according to the embodiment.
FIG. 4(B) is a second diagram illustrating an example of the vibration pattern and the LED blink pattern in the portable electrocardiographic measurement device according to the embodiment.
FIG. 4(C) is a third diagram illustrating an example of the vibration pattern and the LED blink pattern in the portable electrocardiographic measurement device according to the embodiment.
Figure 4:
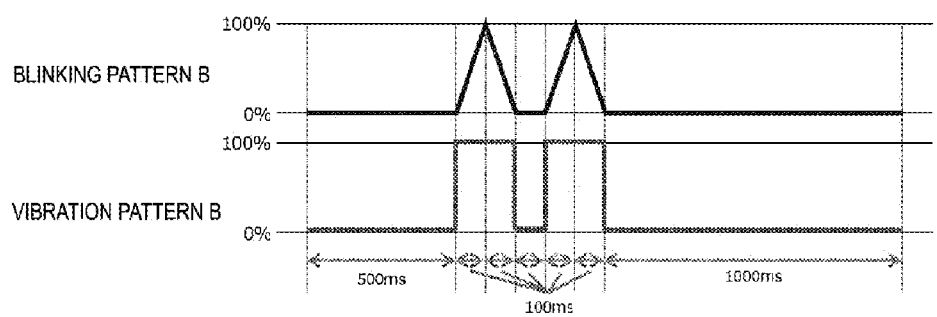
Figure 4:
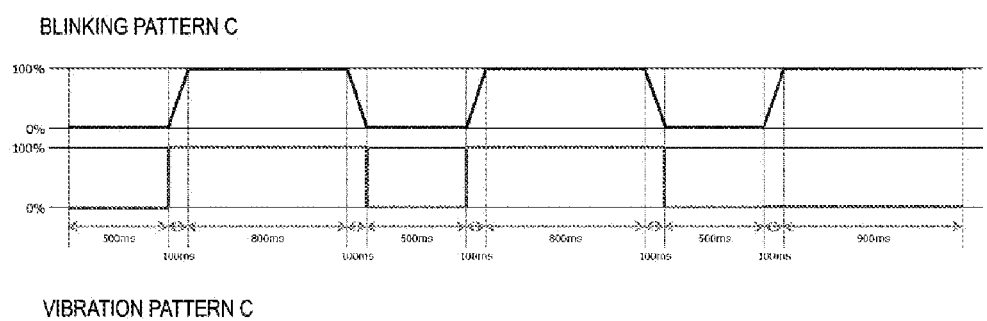

In addition, by blinking the LEDs of the display processing unit 106 (e.g., the measurement state notification LED 13 and the like) in a blinking pattern associated with each vibration pattern, the occurrence and contents of an event related to the electrocardiographic measurement processing can be more clearly recognized. FIG. 4 illustrates an example of the vibration patterns of the vibration processing unit 111 including the patterns A to C and the LED blinking patterns of the display processing unit 106 associated with the respective vibration patterns.

Modification of Measurement Processing

Figure 5:
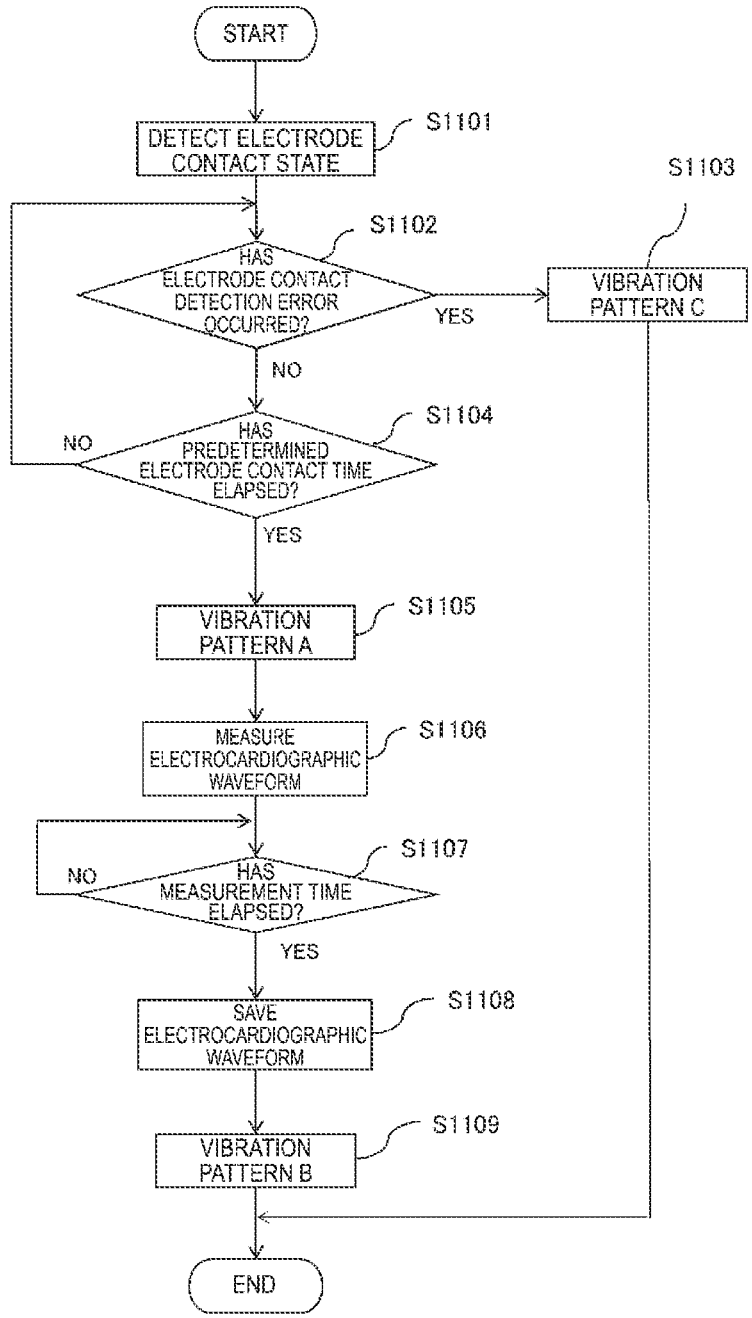
FIG. 5 is a flowchart illustrating another example of the flow of electrocardiographic waveform measurement processing in the portable electrocardiographic measurement device according to the embodiment.

As described above, in response to the successful ending of the analysis of the electrocardiographic waveform data and the ending of saving of the waveform data and the analysis data, the series of processing operations is assumed to be successfully ended and the vibration processing unit 111 is vibrated in the pattern B. However, the timing for vibrating the vibration processing unit 111 in the pattern B is not limited to the above-described timing. An example of another measurement processing of the portable electrocardiograph 10 will be described based on FIG. 5. FIG. 5 is a flowchart illustrating a procedure of processing in a modification executed when electrocardiographic measurement is performed using the portable electrocardiograph 10. Note that, in the description below, components and processing operations similar to those described above are denoted by the same reference numerals, and the description of the components and processing operations is omitted.

As illustrated in FIG. 5, the procedure of measurement processing in the present modification is similar to that in the above-described embodiment from the start of the processing to step S1107. In response to determining that the elapsed time of the electrocardiographic measurement has reached a predetermined value (e.g., 30 seconds), the control processing unit 101 saves the data of the electrocardiographic waveform in the storage processing unit 109 (S1108), and subsequently executes processing for vibrating the vibration processing unit 111 in the pattern B. In other words, in the present modification, the electrocardiographic waveform is not analyzed, and in response to acquiring the electrocardiographic waveform data, the measurement processing is assumed to be successfully ended, and the vibration in the pattern B is used to notify the user of the successful end.

Vibration Notification of Event Related to Communication Settings

The portable electrocardiograph 10 according to the present embodiment can be connected to another information processing terminal for BLE communication with the information processing terminal via the communication processing unit 109. Vibration of the vibration processing unit 111 can also be used to recognize the occurrence and contents of an event related to communication settings for connection to the information processing terminal. In the description below, the operation related to the communication settings in the portable electrocardiograph 10 will be described with reference to FIGS. 6 to 9.

Figure 6:
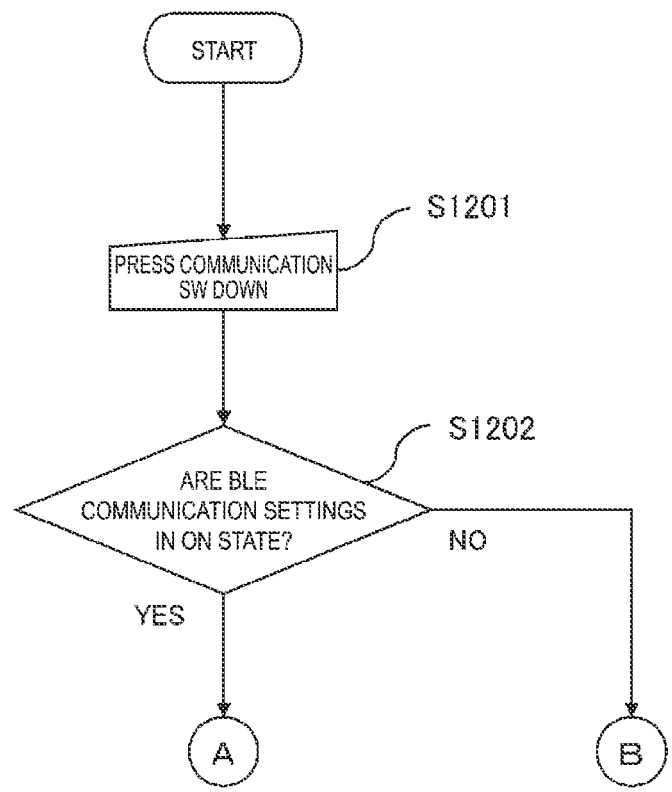
FIG. 6 is a first flowchart related to processing for communication settings in the portable electrocardiographic measurement device according to the embodiment.
Figure 7:
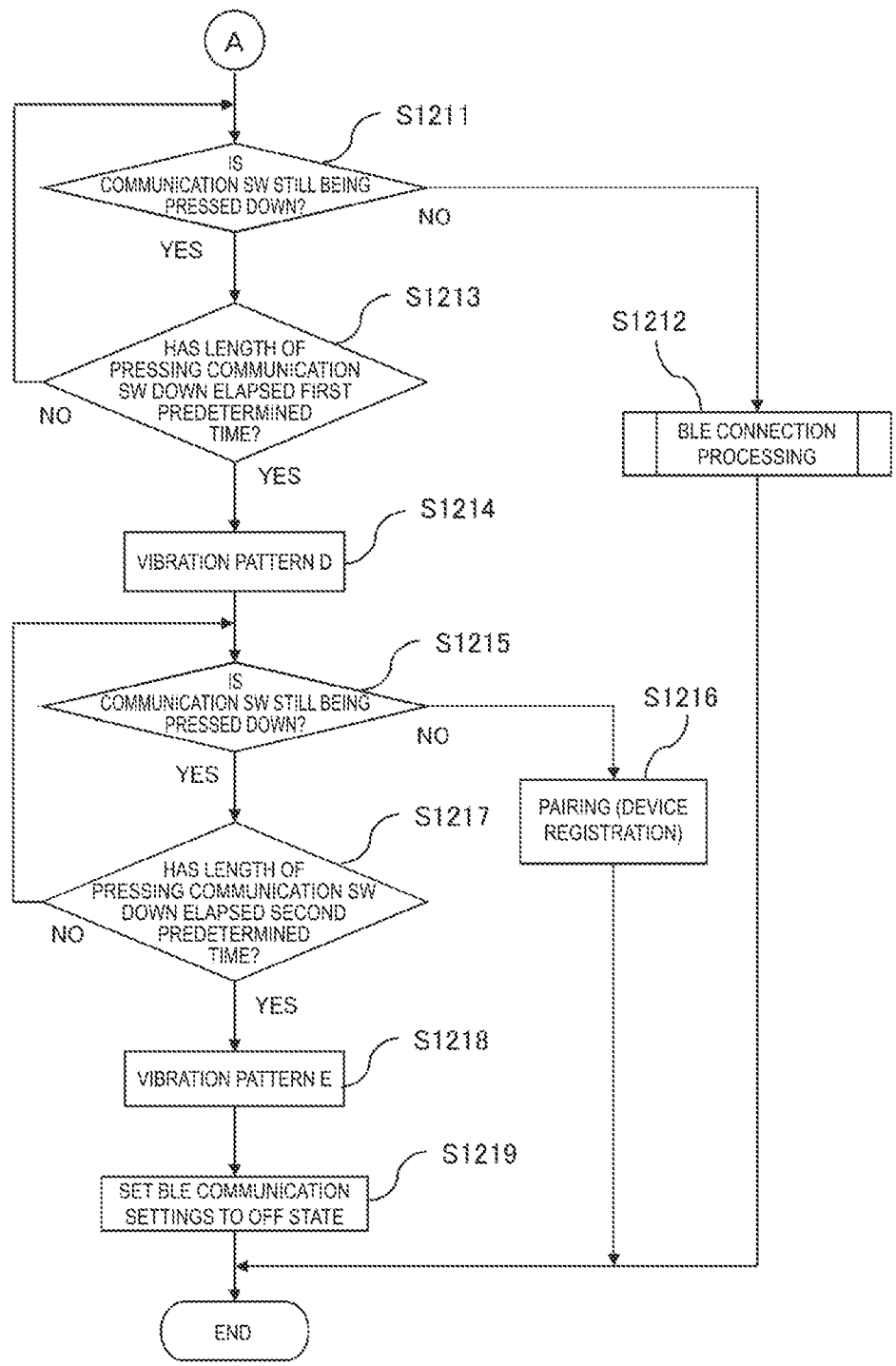
FIG. 7 is a second flowchart related to the processing for communication settings in the portable electrocardiographic measurement device according to the embodiment.
Figure 8:
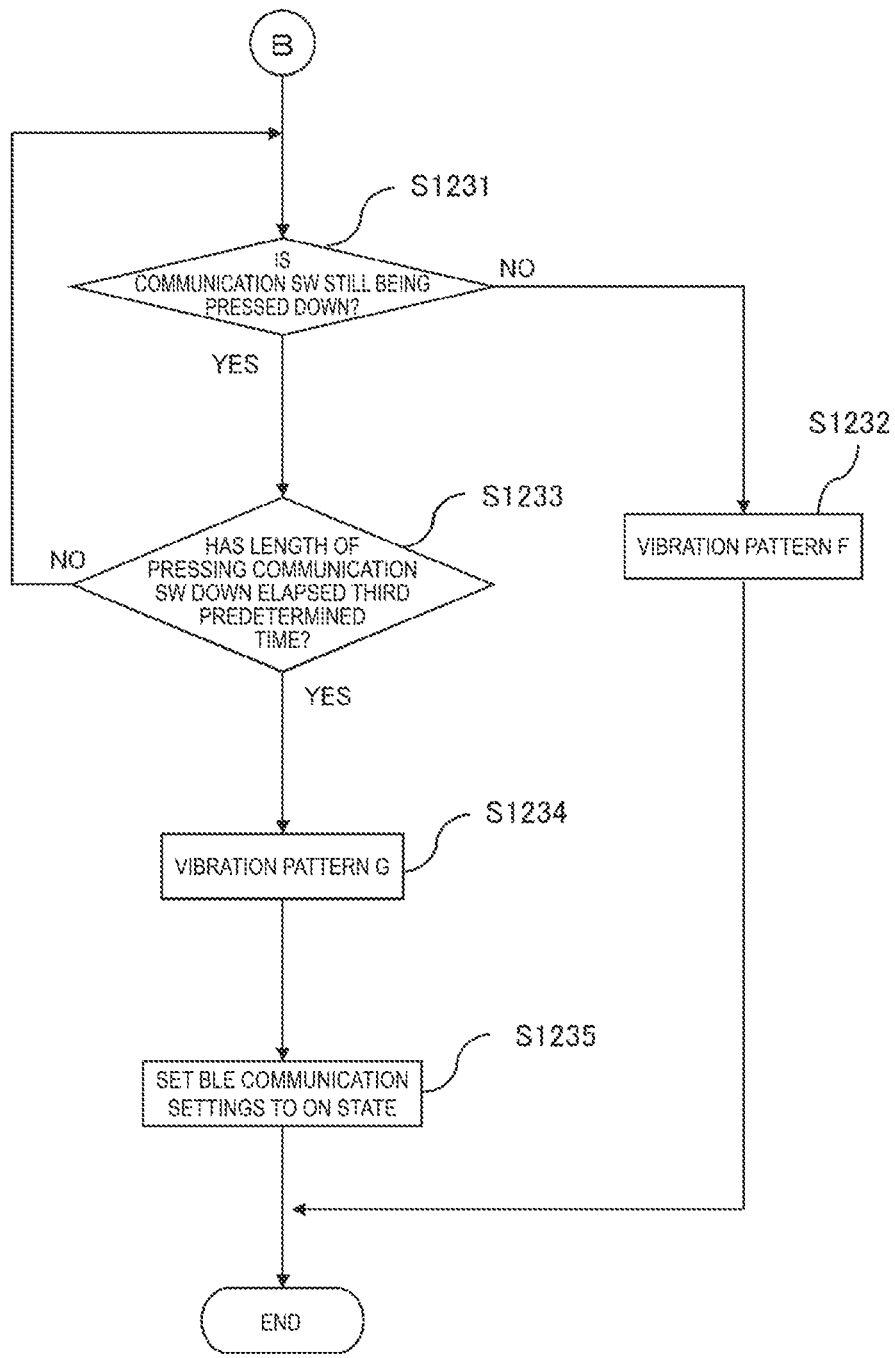
FIG. 8 is a third flowchart related to the processing for communication settings in the portable electrocardiographic measurement device according to the embodiment.

FIGS. 6 to 8 are flowcharts illustrating a processing flow related to the communication settings in the portable electrocardiograph 10. As illustrated in FIG. 6, when the BLE communication button 17 is pressed down by the user (S1201), the control processing unit 101 determines whether BLE communication is enabled in the current communication settings (S1202). Here, in response to determining that the BLE communication is enabled (hereinafter referred to as the state of BLE communication settings ON), the control processing unit 101 proceeds to step S1211 of FIG. 7, and determines whether the BLE communication button 17 is continuously pressed down (a so-called hold-down state) (S1213). Here, in response to determining that the BLE communication button 17 is no longer pressed down, the control processing unit 101 performs a predetermined subroutine related to the BLE connection (S1212), and ends the processing. The predetermined subroutine will be described below.

On the other hand, in response to determining in step S1211 that the BLE communication button 17 is held down, the control processing unit 101 determines whether the length of time of holding down exceeds a first predetermined time (for example, 2 seconds) (S1213). Here, in response to determining that the first predetermined time is not exceeded, the control processing unit 101 returns to step S1211 and repeats the subsequent processing. On the other hand, in response to determining in step S1213 that the first predetermined time is exceeded, the control processing unit 101 causes the communication settings to transition to a pairing (device registration) standby state to vibrate the vibration processing unit 111 in a vibration pattern (hereinafter referred to as a pattern D) meaning the communication settings have transitioned to the pairing standby state (S1214).

Then, the control processing unit 101 executes processing for determining whether the BLE communication button 17 is continuously pressed down (S1215). Here, in response to determining that the BLE communication button 17 is not pressed down, the control processing unit 101 brings the communication settings into a pairing mode (S1216), and ends the series of processing operations. On the other hand, in response to determining in step S1215 that the BLE communication button 17 is held down, the control processing unit 101 determines whether the length of time of holding down exceeds a second predetermined time (e.g., 10 seconds) (S1217).

Here, in response to determining that the second predetermined time is not exceeded, the control processing unit 101 returns to step S1215 and repeats the subsequent processing. On the other hand, in response to determining in step S1217 that the second predetermined time is exceeded, the control processing unit 101 vibrates the vibration processing unit 111 in a vibration pattern (hereinafter referred to as a pattern E) meaning that the communication settings are switched to a state in which the BLE communication is disabled (hereinafter referred to as the BLE communication settings OFF) (S1218), and changes the BLE communication settings to the OFF state to end the series of processing operations (S1219).

Subsequently, a description based on FIG. 8 will be given for processing that is executed in response to the determination in step S1202 that the BLE communication settings are in the OFF state. In response to determining in step S1202 that the BLE communication settings are in the OFF state, the control processing unit 101 determines whether the BLE communication button 17 is held down (step S1231). Here, in response to determining that the BLE communication button 17 is not held down, the control processing unit 101 vibrates the vibration processing unit 111 in a vibration pattern (hereinafter referred to as a pattern F) meaning that the BLE communication settings are in the OFF state (S1232), and ends the series of processing operations.

On the other hand, in response to determining in step S1231 that the BLE communication button 17 is held down, the control processing unit 101 determines whether the length of time of holding down exceeds a third predetermined time (e.g., 5 seconds) (S1233). Here, in response to determining that the third predetermined time is not exceeded, the control processing unit 101 returns to step S1231 and repeats the subsequent processing. On the other hand, in response to determining in step S1233 that the third predetermined time is exceeded, the control processing unit 101 vibrates the vibration processing unit 111 in a vibration pattern (hereinafter referred to as a pattern G) meaning that the communication settings are switched to the BLE communication settings ON (S1234), and changes the BLE communication settings to the ON state. The control processing unit 101 then ends the series of processing operations (S1235).

Figure 9:
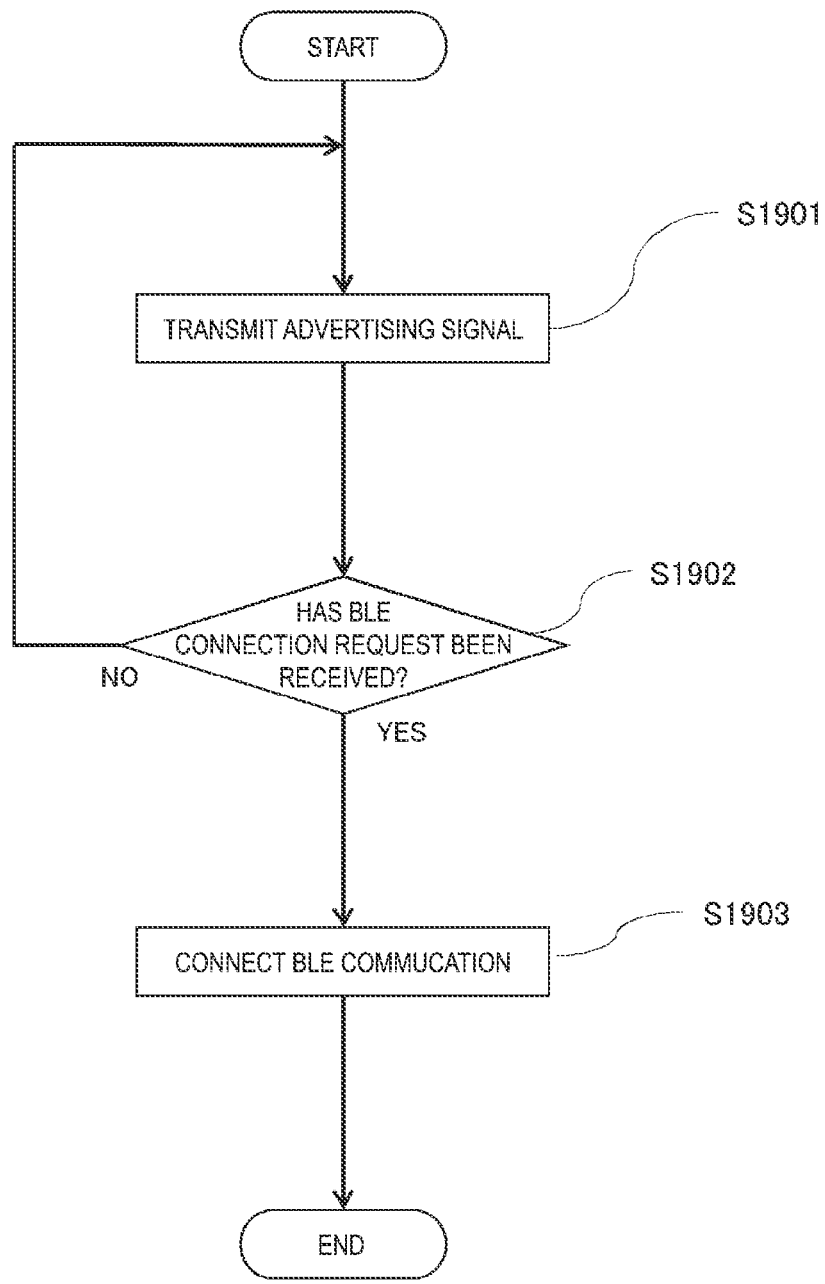
FIG. 9 is a flowchart illustrating a processing subroutine executed when BLE communication is performed by the portable electrocardiographic measurement device according to the embodiment.

Now, the subroutine of step S1212 will be described based on FIG. 9. As illustrated in FIG. 9, the control processing unit 101 first transmits an advertising signal for BLE communication from the communication processing unit 109 (S1901). Then, the control processing unit 101 determines whether a connection request for BLE communication has been received from the information processing terminal (S1902). Here, in response to determining that no connection request for BLE communication has been received, the control processing unit 101 repeats similar processing until the BLE communication processing is canceled due to the elapse of a predetermined time or operation of the operation unit 107. On the other hand, in response to determining that a connection request for BLE communication has been received, the control processing unit 101 proceeds to step S1903, and makes BLE connection to a device transmitting the connection request. When the BLE communication connection is established, the control processing unit 101 ends the subroutine.

As described above, the portable electrocardiograph 10 according to the present embodiment also allows the occurrence and contents of an event related to communication settings for connection to the information processing terminal to be recognized from a difference in the pattern of vibration of the vibration processing unit 111 (patterns D to G). For example, the BLE communication LED 17a may be blinked in a blinking pattern associated with each of the vibration patterns. In this way, the occurrence and contents of an event related to the communication settings can be more clearly recognized.

Vibration Notification of Other Events

Figure 10:
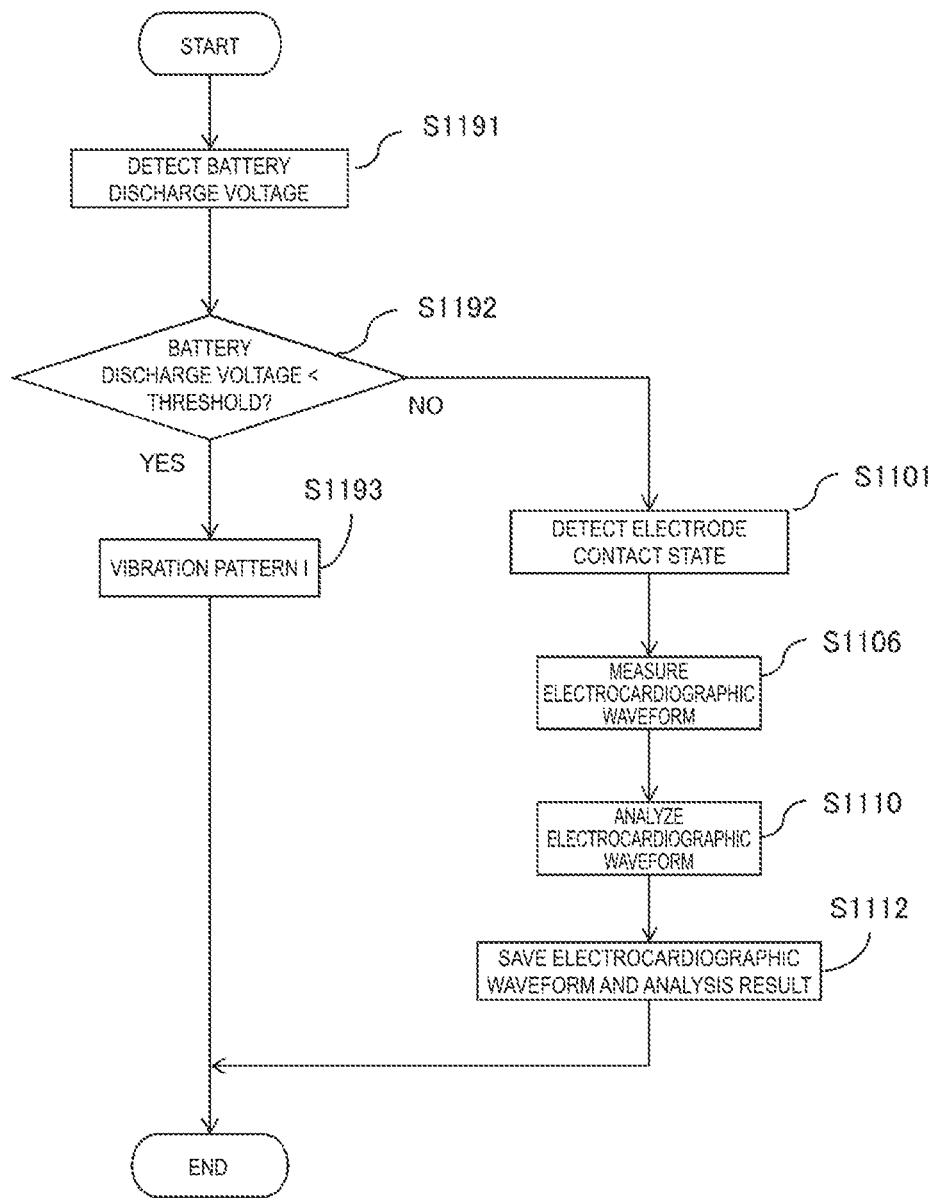
FIG. 10 is a flow chart illustrating another example of the flow of electrocardiographic waveform measurement processing in the portable electrocardiographic measurement device according to the embodiment.

The notification of the contents of an event based on the vibration of the vibration processing unit 111 and differences in the vibration pattern can be applied to the notification of other events according to the portable electrocardiograph 10. As an example, a description based on FIG. 10 will be given for processing for informing, by vibration of the vibration processing unit 111, a decrease in the discharge voltage of a battery used as a power source. FIG. 10 is a flowchart illustrating a flow of operations of giving notice of the discharge voltage of the battery by vibration of the vibration processing unit 111.

When the measurement switch 16 is pressed down by the user, the control processing unit 101 first executes processing for acquiring the discharge voltage of the battery (S1191). Then, the control processing unit 101 determines whether the discharge voltage acquired is lower than a predetermined threshold (S1192), and in response to determining that the discharge voltage is lower than the predetermined threshold, the control processing unit 101 vibrates the vibration processing unit 111 in a vibration pattern (hereinafter referred to as a pattern I) meaning that the battery voltage is reduced (S1193), and ends the processing. On the other hand, in response to determining in step S1192 that the discharge voltage of the battery is equal to or greater than the threshold, the control processing unit 101 executes the measurement processing for the electrocardiographic waveform described above (S1101, S1106, S1110, and S1112).

Note that in step S1193, for example, the battery change LED 19 may be blinked in a blinking pattern associated with the pattern I. Additionally, the battery change LED 19 may be always on until the battery is changed.

Second Embodiment

As in the first embodiment, the portable electrocardiograph 10 can singularly perform electrocardiographic measurement, analysis of the measurement data, and display of the analysis result. However, by communicatively connecting the portable electrocardiograph 10 to the information processing terminal, the convenience of the portable electrocardiograph 10 can be further improved. Based on FIGS. 11 to 16, description will be given below for an embodiment of an information management system 1 including the portable electrocardiograph 10 and a smart phone 20 corresponding to an example of the information processing terminal.

Figure 11:
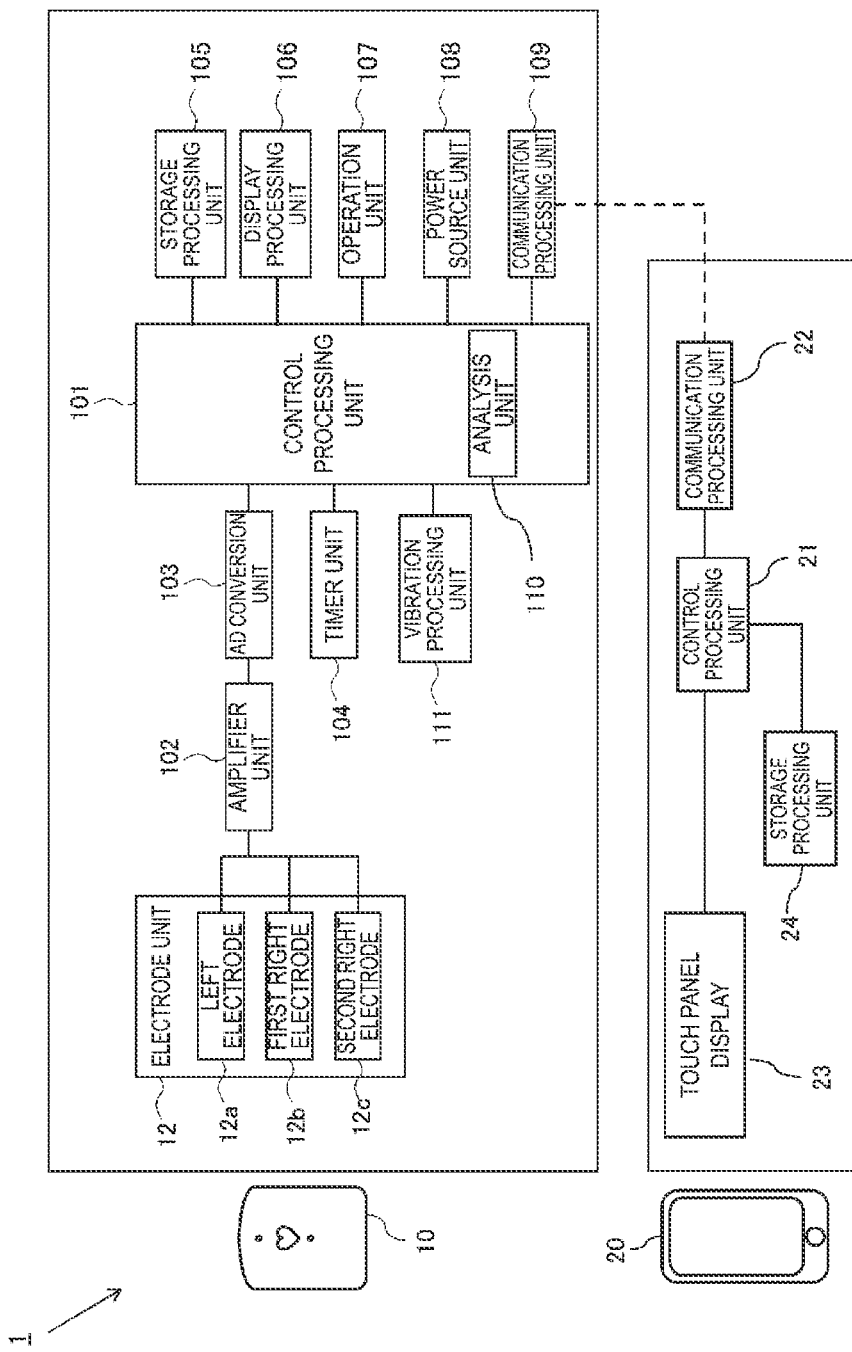
FIG. 11 is a block diagram illustrating an overview of an information management system according to an embodiment.

FIG. 11 is a schematic diagram illustrating a configuration example of the information management system 1 according to the present embodiment. As illustrated in FIG. 11, the information management system 1 includes the portable electrocardiograph 10 and the smart phone 20, which are communicatively connected. Note that the portable electrocardiograph 10 is configured similarly to that described in the first embodiment, and will thus not be described.

Information Processing Terminal

As illustrated in FIG. 11, the smart phone 20, corresponding to an example of the information processing terminal, includes a control processing unit 21, a communication processing unit 22, a touch panel display 23, and a storage processing unit 24. The control processing unit 21 manages the control of the smart phone 20, and includes, for example, a CPU and the like. The control processing unit executes various programs stored in the storage processing unit 24 to fulfill functions corresponding to the programs. The communication processing unit 22 includes an antenna for wireless communication, and is a function of communicating with another device such as the portable electrocardiograph 10, and a wireless base station. Also, the communication processing unit 22 may include a terminal for wired communication.

The touch panel display 23 plays both a role of a display unit which is an aspect of an output unit, and a role of an input unit, and as described below, in a case where communicative connection to the portable electrocardiograph 10 is established, the touch panel display 23 can display status information such as the remaining time until the end of measurement, graph data of the electrocardiographic waveform, and the like. In addition, operations from the user are received via various input images.

The storage processing unit 24 includes, for example, a long-term storage medium such as a flash memory in addition to a main memory such as a RAM, and stores various information such as application programs, measurement electrocardiographic waveforms, and analysis results.

Figure 12:
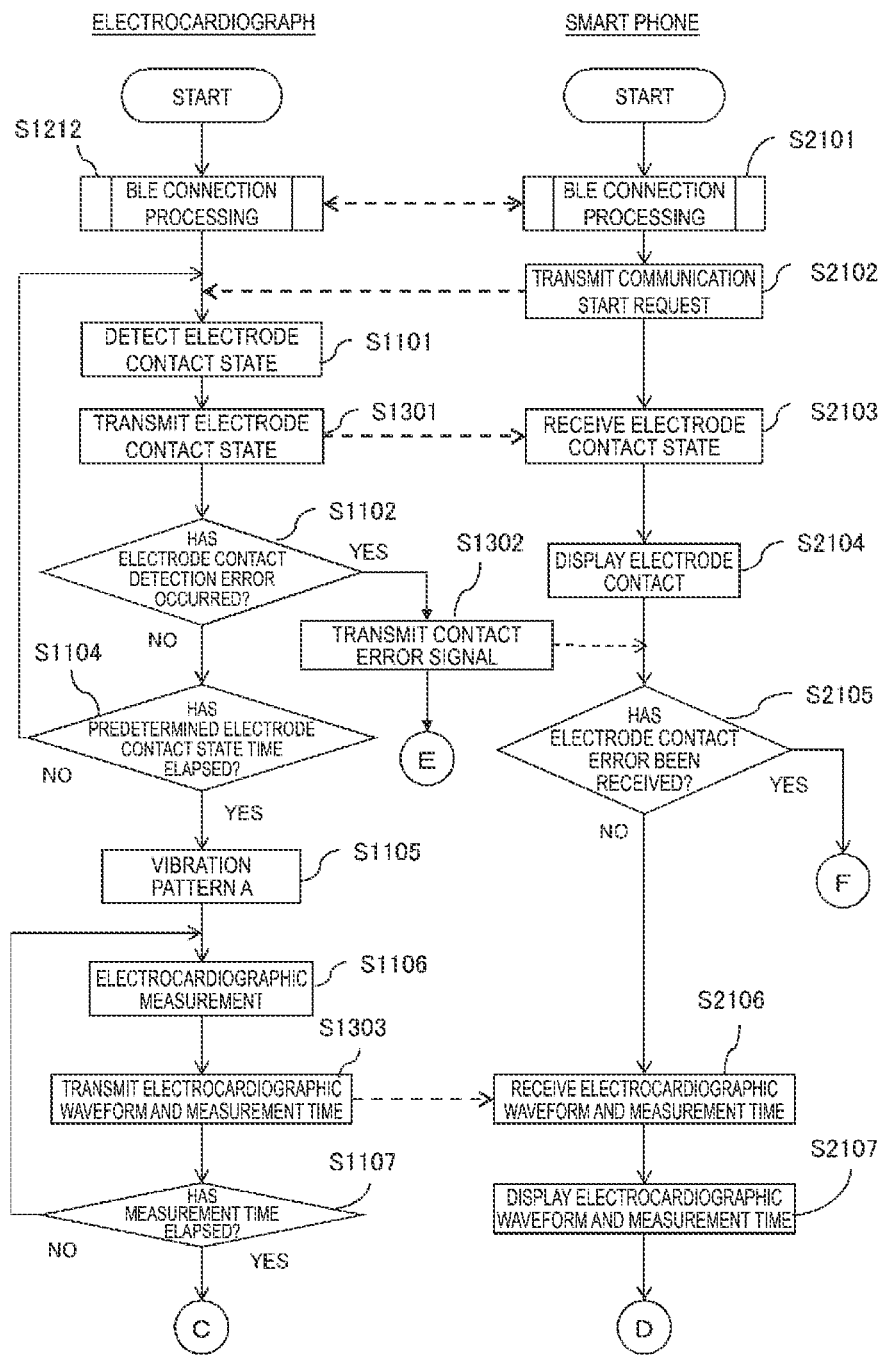
FIG. 12 is a first flowchart illustrating parts of processing flows of a portable electrocardiograph and a smart phone communicatively connected in the information management system according to the embodiment.
Figure 13:
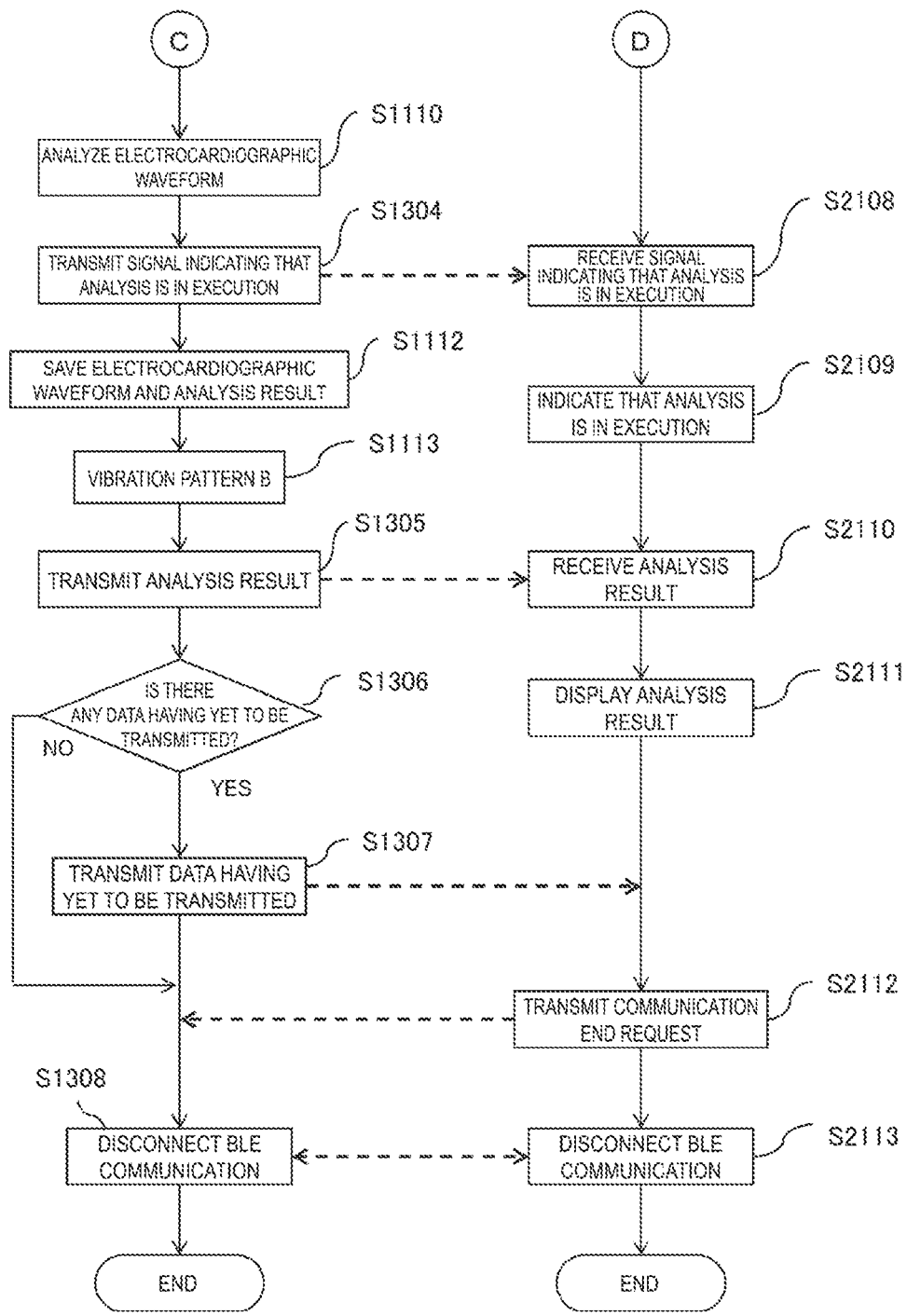
FIG. 13 is a second flowchart illustrating parts of the processing flows of the portable electrocardiograph and the smart phone communicatively connected in the information management system according to the embodiment.
Figure 14:
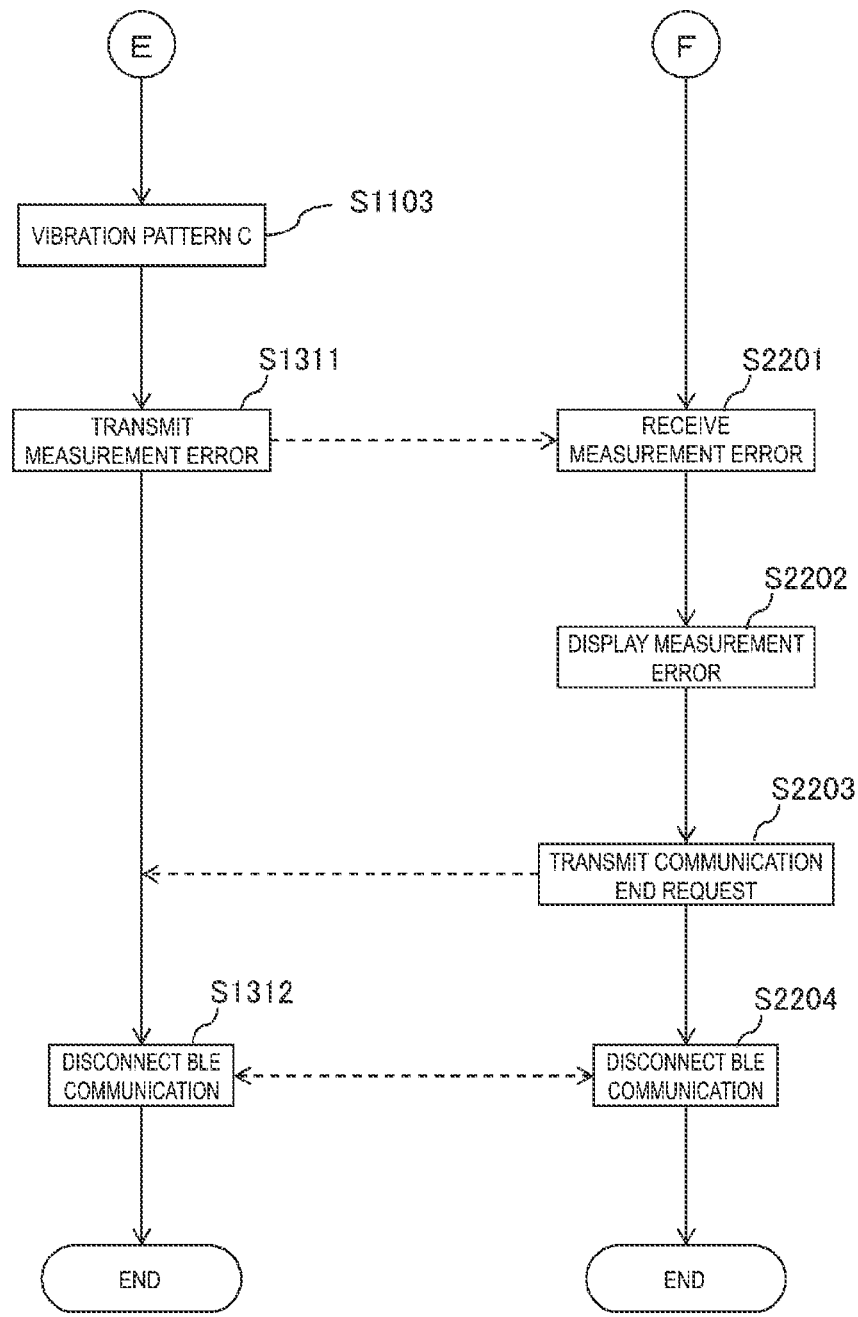
FIG. 14 is a third flowchart illustrating parts of the processing flows of the portable electrocardiograph and the smart phone communicatively connected in the information management system according to the embodiment.

In the description below, a description based on FIGS. 12 to 14 will be given for processing that is executed in a case where electrocardiographic measurement is performed by allowing the portable electrocardiograph 10 and the smart phone 20 to cooperate with each other through BLE communication. FIGS. 12 to 14 are diagrams illustrating the flow of processing of each of the portable electrocardiograph 10 and the smart phone 20 connected to each other through BLE communication and also illustrating timings for transmitting information between the devices. Note that for the flow of the processing of the portable electrocardiograph 10, the above-described processing operations are denoted by the same reference numerals, and the detailed description of the processing operations is omitted.

First, with the portable electrocardiograph 10 in the BLE communication settings ON state, the user presses the BLE communication button 17 down, and the control processing unit 101 executes the processing of the subroutine for BLE communication (S1212). The subroutine is as described above.

Additionally, the user enables the smart phone 20 to make BLE communication with the portable electrocardiograph 10. Specifically, the user operates the touch panel display 23 to set the BLE connection settings to the ON state in a setting menu or the like. Alternatively, the BLE connection settings may be set to the ON state by initiating a dedicated application program for cooperation with the portable electrocardiograph 10.

Figure 15:
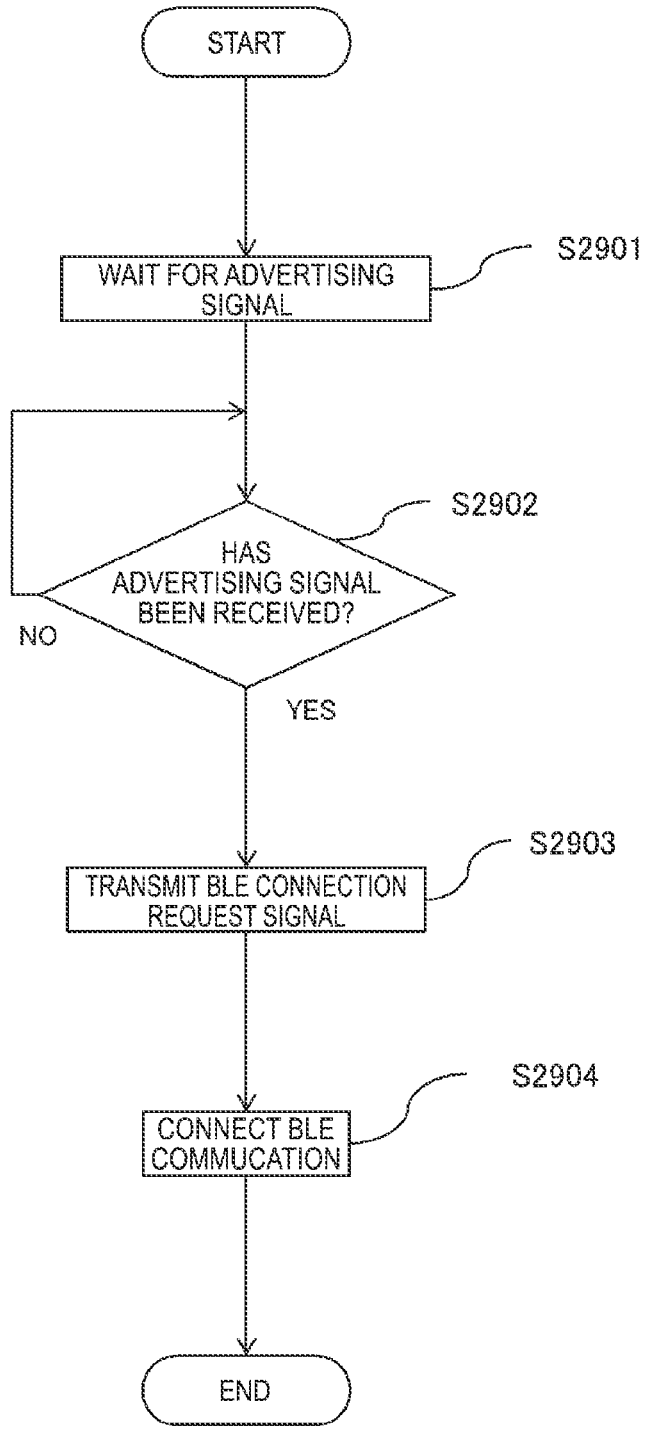
FIG. 15 is a flowchart illustrating a processing subroutine executed when BLE communication is performed by the information processing terminal according to the embodiment.

When the BLE connection settings are set to the ON state, the control processing unit 21 of the smart phone 20 executes the subroutine for BLE connection via the communication processing unit 22 (S2101). FIG. 15 illustrates the processing of the sub-routine. Specifically, when the subroutine is initiated, the control processing unit 21 waits to receive the advertising signal from the portable electrocardiograph 10 (S2901). Then, the control processing unit 21 determines whether the advertisement signal has been received (S2902), and repeats the processing until the control processing unit 21 determines that the signal has been received. In response to determining in step S2092 that the advertising signal is received, the control processing unit 21 transmits a BLE connection request signal to the portable electrocardiograph 10 via the communication processing unit 22 (S2903). Then, the control processing unit 21 makes BLE connection to the portable electrocardiograph 10 (S2904. Corresponding to S1903 described above), and ends the subroutine. Then, in step S2102 in FIG. 12, the control processing unit 21 transmits a communication start request to the portable electrocardiograph 10.

On the other hand, the control processing unit 101 of the portable electrocardiograph 10 detects an electrode contact state (S1101), and then transmits information related to the electrode contact state to the smart phone 20 (S1301), and the smart phone 20 receives the information (S2103).

The smart phone 20, having received the information of the electrode contact state, displays the electrode contact state on the touch panel display 23 (S2104). The smart phone 20 may display, for example, the message "The electrodes are in proper contact", "The electrodes are not in proper contact", or the like.

After step S1301, the control processing unit 101 of the portable electrocardiograph 10 executes processing for determining the presence or absence of an electrode contact error (S1102). Here, in response to determining that an error is occurring, the control processing unit 101 transmits an electrode contact error signal to the smart phone (S1302), and proceeds to step S1103 in FIG. 14 to vibrate the vibration processing unit 111 in the pattern C, and transmits, to the smart phone 20, a signal indicating that the measurement is not successfully ended (S1311).

On the other hand, after step S2104, the smart phone 20 determines whether the electrode contact error signal has been received from the portable electrocardiograph 10 (S2105), and in response to determining that the electrode contact error has been received, the smart phone 20 proceeds to step S2201 in FIG. 14, and further receives a signal indicating that the measurement is not successfully ended. Then, the smart phone 20 indicates, on the touch panel display 23, that the measurement is not successfully ended, and transmits, to the portable electrocardiograph 10, a signal requesting the end of communication (S2203). Subsequently, the portable electrocardiograph 10 and the smart phone 20 disconnect the BLE connection (S1312 and S2204), and end the series of processing operations.

In step S1102, in response to determining that no contact detection error has occurred, the control processing unit 101 of the portable electrocardiograph 10 then executes processing for determining whether a predetermined time has elapsed with the electrodes in proper contact (S1104). Here, in response to determining that the predetermined time has not elapsed, then the control processing unit 101 returns to step S1101, and repeats similar processing. On the other hand, in response to determining that the predetermined time has elapsed, the control processing unit 101 vibrates the vibration processing unit 111 in the pattern A (S1105), and executes the actual electrocardiographic measurement (S1106). Then, the control processing unit 101 executes processing for transmitting to the smart phone 20 the data of the measured electrocardiographic waveform and the electrocardiographic measurement time (the remaining time until the end of the measurement) (S1303).

The data transmitted from the portable electrocardiograph 10 in step S1303 is received in the smart phone 20 (S2106), and the electrocardiographic measurement time and the electrocardiographic waveform graph are displayed on the touch panel display 23 (S2107). Specifically, the graph of the electrocardiographic waveform may be displayed along with, for example, the countdown message "XX seconds until the end of the electrocardiographic measurement".

Then, in step S1107, the control processing unit 101 of the portable electrocardiograph 10 determines whether a predetermined measurement time has elapsed, and in response to determining that the predetermined time has not elapsed, returns to step S1106 and repeats the subsequent processing. On the other hand, in response to determining in step S1107 that the predetermined measurement time has elapsed, the control processing unit 101 proceeds to step S1110 in FIG. 13, and the analysis unit 110 analyzes the electrocardiographic waveform (S1303). Then, while smart phone analysis is being performed, the control processing unit 101 transmits, to the 20, a signal indicating that analysis is being performed (S1304). In response to ending of the analysis, the control processing unit 101 saves an analysis result and data of an electrocardiographic waveform in the storage processing unit 105 (S1112), and vibrates the vibration processing unit 111 in the pattern B.

Furthermore, the control processing unit 101 transmits the analysis result information to the smart phone 20 (S1305), and determines whether any data (electrocardiographic waveform, analysis result) has yet to be transmitted to the smart phone 20 (S1306). Here, in response to determining that any data has yet to be transmitted, the control processing unit 101 transmits the data to the smart phone 20 (S1307), waits for a communication end request from the smart phone 20, and disconnects the BLE connection (S1308) to end the series of processing operations. Note that in response to determining in step S1306 that no data has yet to be transmitted, the control processing unit 101 skips the processing of step S1307 and proceeds to step S1308.

After step S2107, in response to receiving, via the communication processing unit 22, information indicating that the electrocardiographic waveform is being analyzed (S2108), the control processing unit 21 of the smart phone 20 displays the information on the touch panel display 23 (S2109). Then, in response to receiving, via the communication processing unit 22, the analysis result information transmitted from the portable electrocardiograph 10 (S2110), the control processing unit 21 causes the touch panel display 23 to display the result (S2111).

Subsequently, in a case where data having yet to be transmitted is transmitted from the portable electrocardiograph 10, the control processing unit 21 receives the data and transmits, to the portable electrocardiograph 10, a signal requesting the end of the communication (S2112), and deletes the BLE connection (S2113) to end the series of processing operations.

As is described above, the portable electrocardiograph 10 and the information management system 1 of the present embodiment can be used in cooperation with an information processing terminal such as the smart phone 20 to display various data such as electrocardiographic waveform data on the display for browsing. Additionally, the data received can be saved, and can be effectively utilized by using an application program or the like.

Vibration Notification Provided when Communication Error Occurs

Figure 16:
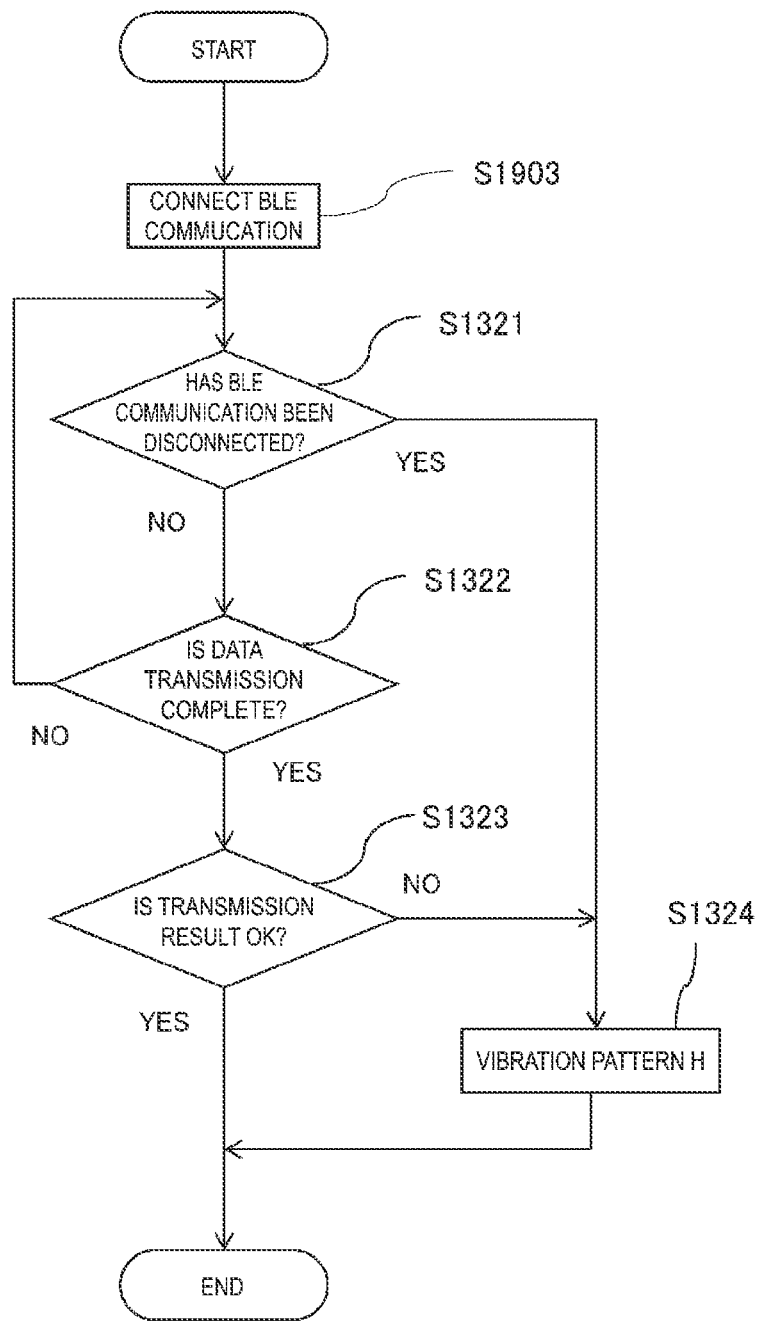
FIG. 16 is a flowchart illustrating a processing flow executed when communication errors are managed in the portable electrocardiographic measurement device according to the embodiment.

Note that in the present embodiment, even in a case where a communication error occurs between the portable electrocardiograph 10 and the smart phone 20, the user can be notified of the communication error by vibrating the vibration processing unit 111 of the portable electrocardiograph 10 in a predetermined vibration pattern. The flow of processing executed in that case will be described based on FIG. 16. FIG. 16 is a flowchart illustrating operations performed in a case where an error occurs in BLE communication between the portable electrocardiograph 10 and the smart phone 20.

As illustrated in FIG. 16, when the BLE connection is made (S1903), the control processing unit 101 of the portable electrocardiograph 10 determines whether the BLE communication has been disconnected by using disconnection processing that is not normal (S1321). Here, in response to determining that the BLE communication has been disconnected by using disconnection processing that is not normal, the control processing unit 101 vibrates the vibration processing unit 111 in a vibration pattern (hereinafter referred to as a pattern H) meaning that a communication error has occurred (S1324), and ends the processing.

On the other hand, in response to determining in step S1321 that the BLE communication is not disconnected, the control processing unit 101 determines whether all of the data to be transmitted to the smart phone 20 such as the electrocardiographic waveform data and analysis result has been successfully transmitted (S1322). Here, in response to determining that not all of the data has been successfully transmitted, then the control processing unit 101 returns to step S1321 and repeats the subsequent processing. On the other hand, in response to determining in step S1322 that all of the data has been transmitted, the control processing unit 101 determines whether there is a problem with the transmission result (i.e., whether an error has occurred during transmission) (S1323). Here, in response to determining that there is no problem with the transmission result, the control processing unit 101 ends the processing without taking any action. On the other hand, in step S1323, in response to determining that a transmission error has occurred, the control processing unit 101 vibrates the vibration processing unit 111 in the vibration pattern of the pattern H (S1324), and ends the processing.

With such a configuration, in a case where an error occurs in communication with the smart phone 20 even though the measurement processing itself is not abnormal, the user can know the occurrence of the communication error by the vibration pattern indicating that a communication error has occurred. Additionally, for example, by blinking the BLE communication LED 17a in a blinking pattern associated with the vibration in the pattern H, the occurrence of the communication error can be more clearly recognized.

Other Points

The description of each example described above is merely illustrative of the present invention, and the present invention is not limited to the specific embodiments described above. Within the scope of the technical idea of the present invention, various modifications and combinations may be made.

For example, the information processing terminal is not limited to a smart phone, and may be another portable information processing terminal such as a tablet terminal, or may be a stationary terminal. Additionally, the communication processing unit is not limited to a communication unit intended for BLE communication, and may be an antenna enabling other wireless communication such as Wi-Fi (trade name) or infrared communication. Alternatively, the communication unit may communicate using wired connection.

REFERENCE NUMERALS LIST

1 Biological information management system
10 Portable electrocardiograph
12a Left electrode
12b First right electrode
12c Second right electrode
13 Measurement state notification LED
14 Analysis result notification LED
15 Battery cover
16 Measurement switch
16a Measurement mode LED
17 Communication button
17a BLE Communication LED
18 Available memory display LED
19 Battery change LED
20 Smart phone

The invention claimed is:

1. A portable electrocardiographic waveform measurement device using a battery as a power source, the device comprising:
   a plurality of electrodes configured to measure an electrocardiographic waveform;
   a vibration unit configured to generate vibration;
   a control unit configured to execute measurement processing for the electrocardiographic waveform; and
   an LED display unit, wherein the control unit blinks the LED display unit in a predetermined blinking pattern associated with each of the vibration patterns when the control unit vibrates the vibration unit, vibrates the vibration unit in a first vibration pattern when the measurement processing for the electrocardiographic waveform is started, and vibrates the vibration unit in a second vibration pattern when the measurement processing for the electrocardiographic waveform is ended.

2. The portable electrocardiographic waveform measurement device according to claim 1, wherein the control unit vibrates the vibration unit in a third vibration pattern in a case where the measurement processing for the electrocardiographic waveform fails to complete successfully.

3. The portable electrocardiographic waveform measurement device according to claim 1, further comprising a communication unit configured to communicate with the information processing terminal, wherein the control unit further executes communication processing with the information processing terminal, and vibrates the vibration unit in a fourth vibration pattern in a case where an abnormality occurs in communication with the information processing terminal during the communication processing.

4. The portable electrocardiographic waveform measurement device according to claim 3, wherein the control unit further executes communication setting processing for switching the communication unit between an ON state in which communication is enabled and an OFF state in which communication is disabled.

5. The portable electrocardiographic waveform measurement device according to claim 4, wherein the control unit vibrates the vibration unit in a fifth vibration pattern in a case where the control unit executes the processing for switching the communication unit to the ON state.

6. The portable electrocardiographic waveform measurement device according to claim 4, wherein the control unit vibrates the vibration unit in a sixth vibration pattern in a case where the control unit executes the processing for switching the communication unit to the OFF state.

7. The portable electrocardiographic waveform measurement device according to claim 4, further comprising an input unit configured to receive input from a user, wherein the control unit vibrates the vibration unit in a seventh vibration pattern in a case where the communication unit is in the OFF state when the control unit receives, via the input unit, an indication to execute the communication processing.

8. The portable electrocardiographic waveform measurement device according to claim 3, further comprising a storage unit configured to store at least information for device registration for the information processing terminal, and the control unit further executes pairing processing for device registration of the information processing terminal, and vibrates the vibration unit in an eighth vibration pattern when the pairing processing is started.

9. The portable electrocardiographic waveform measurement device according to claim 1, wherein the control unit vibrates the vibration unit in a ninth vibration pattern in a case where a discharge voltage of the battery is equal to or less than a predetermined threshold.

10. An information management system comprising:

the portable electrocardiographic waveform measurement device according to claim 3; and, an information processing terminal comprising a communication unit configured to communicate with the portable electrocardiographic waveform measurement device.

* * * * *